United States Patent [19]

Hoppert et al.

[11] 4,013,519

[45] Mar. 22, 1977

[54] RECOVERY METHOD FOR POLYESTER STILL BOTTOMS

[75] Inventors: Bruce Noel Hoppert; Alfred Berghausen, III, both of Cincinnati, Ohio

[73] Assignee: Safetech, Inc., Cincinnati, Ohio

[22] Filed: Mar. 25, 1976

[21] Appl. No.: 670,123

[52] U.S. Cl. .................................... 203/33; 210/51; 210/53; 203/34; 203/37; 203/41; 260/637 R; 260/525; 423/617; 203/38

[51] Int. Cl.² .................... B01D 21/01; C07C 29/26

[58] Field of Search .................. 203/18, 34, 36, 47, 203/33, 37, 41, 38; 210/42 R, 45, 51–53; 423/87, 617; 260/637 R, 525, 75 HB, 75 T

[56] References Cited

UNITED STATES PATENTS

| | | | |
|---|---|---|---|
| 2,788,373 | 4/1957 | Mills | 260/637 |
| 2,793,235 | 5/1957 | Jenkinson | 260/637 |
| 2,960,447 | 11/1960 | Anderson | 203/64 |
| 3,120,561 | 2/1964 | Fernand | 260/515 |
| 3,317,519 | 5/1967 | Lazarus | 260/239.3 |
| 3,367,847 | 2/1968 | Pierson | 260/637 R |
| 3,525,774 | 8/1970 | Clarke | 260/637 |

OTHER PUBLICATIONS

Qualitative Chemical Analysis, Prescott 5th Ed., D. Van Nostrand Co. N.Y. 1901.

*Primary Examiner*—Hiram H. Bernstein

[57] ABSTRACT

A recovery method by means of which an antimony compound is separated from polyester still bottoms. If desired, the method can be employed so as to recover in usable form, the antimony compound, and the monomers polymerized to produce the polyester.

5 Claims, No Drawings

RECOVERY METHOD FOR POLYESTER STILL BOTTOMS

BACKGROUND OF THE INVENTION AND OBJECTIVES

This invention is directed to a recovery method for still bottom residues produced by the distillation of the spent or excess glycol resulting from the manufacture of polyethylene terephthalic by means of which antimony compound(s) that are present may be separated and, if desired, the monomers may be recovered and converted into usable materials of commercial value.

In recent years, the manufacture of synthetic fibers has grown from a point where such fibers were totally unknown to the current point in time where such fibers constitute a substantial, if not major, portion of fibers used today. Such synthetic fibers have, of course, supplanted to a large degree the use of natural fibers, such as cotton and wool, in the manufacture of clothing and other fabric products. Such synthetic fibers include polyester fibers. The recovery method of this invention is particularly directed to the recovery of materials that are normally waste by-products produced in the polyester manufacturing process.

While the production of polyethylene terephthalate resins is carried out by a number of proprietary processes, there are areas in which the methods are essentially the same. Normally dimethyl terephthalate (DMT) or terephthalic acid (TPA) is condensed with ethylene glycol to form the diglycol ester. Thereafter, in the presence of a catalyst and an increased temperature and pressure the polyethylene terephthalate is produced by splitting of methanol or water. One of the most widely used catalysts employed is antimony trioxide. Inherent in most of the processes is the recovery of the excess or "spent" glycol, normally by distillation, which, by this time is contaminated with, among other things, low molecular weight polyester chains, antimony oxide, DMT and terephthalic acid. See U.S. Pat. Nos. 2,788,373, 2,793,235 and 3,311,544 for such processes and other typical spent glycol recovery processes.

As the ethylene glycol (in the mono, di and tri forms) is fractionally distilled, most of the residual impurities remain in the bottom of the still taking the form of a waxy granular mass which is then removed as a waste material for disposal.

A typical analysis of such a still bottom, including added water and a small amount of sodium hydroxide to make the material handleable is as follows:

| | |
|---|---|
| Water | 26 % |
| Solids | 32 % |
| Ethylene Glycol | 36 % |
| Di Ethylene Glycol | 4.25 % |
| Tri Ethylene Glycol | .75 % |
| Antimony | 7200 PPM |
| Sodium | 4300 PPM |

While the still bottoms described have, in the past, been disposed of by burying or dumping into a waterway, the Environmental Protection Agency has taken the position that the presence of antimony constitutes an environmental and subsequent health hazard. A maximum acceptable limit of 5 PPM of antimony has been established by the Environmental Protection Agency for effluent discharged into a waterway.

Burying can no longer be considered an acceptable disposal because the hazardous metals can leach or drain into a water supply. Pretreating for burying to insure against this or, alternatively, encasing the material becomes enormously expensive and unacceptable as a solution.

Incineration without costly accumulators and stack scrubbers simply puts the hazardous metal into the atmosphere. Ocean dumping is simply another form of waterway contamination and has a deleterious effect on marine life as well as human environment.

No known process presently exists for converting the various materials constituting the still bottoms into articles of commerce by a commercially feasible process.

It has been an objective of this invention to provide a method that will remove antimony compound(s) from polyester still bottoms.

It has been one objective of this invention to provide a recovery method for glycol distillation waste products that permits the recovery of all glycols contained in the low molecular weight polyester solids, as well as the free glycol present in still bottoms, in substantially pure form, uncontaminated by antimony.

It has been another objective of this invention to provide a recovery method of glycol distillation waste products that permits, from a commercially practical standpoint, the free terephthalic acid and the terephthalic acid to be removed from the low molecular weight polyester solid fraction in the still bottom, in substantially pure form, uncontaminated by antimony.

It has been still a further objective of this invention to provide a recovery method for glycol distillation waste products that permits separation, recovery and purification of substantially all of the antimony compound(s) contained in the still bottoms.

These objectives, taken in combination, permit the breakdown and recovery of all the usable base materials found in the still bottoms residue resulting from the distillation of spent glycol, and allows those basic raw materials to be recycled into commerce for use either once again in polyester manufacturing, or in other uses. Under certain conditions it may only be desired to remove the antimony present in the still bottoms without recovering the glycols and terephthalic acid.

GENERAL SUMMARY OF THE INVENTION

In the preferred practice of the process, when it is desired to recover terephthalic acid, ethylene glycol and antimony from the still bottom waste materials, the following general procedure is employed.

1. A predetermined amount of still bottom waste material taken with a predetermined amount of water, if required, is subjected to an alkaline hydrolysis step at a temperature of about 185° to 212° F. to split the low molecular polyester material present into the salts of terephthalic acid and ethylene glycol (as used herein to mean mono, di or tri ethylene glycol).

2. The material resulting from step 1 above is acidified to a pH of about 6.2 to 6.5 forming a precipitate of antimony and/or antimony compounds which are removed and recycled to an antimony production facility.

3. The filtrate from step 2 is subjected to a color removal step using, but not limited to, a material such as carbon.

4. The filtrate from step 3 heated to about 170° F. is acidified to a pH of about 1 to 3 so as to precipitate terephthalic acid out of the filtrate and the precipitated terephthalic acid is filtered, washed and dried. The terephthalic acid is substantially pure and may be sold in commerce, recycled for use in the polyester manufacturing process, etc.

5. To the filtrate from step 4 heated to about 170° to 212° F. is added a material such as, but not limited to, sodium thiosulfate to convert the antimony and/or antimony compound in the filtrate to antimony sulfide. As used hereinafter antimony compounds is meant to include antimony and/or one or more compounds thereof.

6. The material is then filtered to remove the antimony sulfide precipitate leaving a filtrate consisting essentially of ethylene glycol, water, sodium sulfate, and perhaps, sodium bisulfate.

7. Some of the water from the material under step 5 is then removed.

8. To the filtrate from step 7 is added a base to provide a pH of about 6.5 to 8. At this point, if desired, step 3 may be repeated.

9. One of the many ways to those skilled in the art of separating and purifying ethylene glycol is to add a solvent to the material from step 8 to precipitate sodium sulfate.

10. The sodium sulfate precipitate is removed by filtering, for example, and is washed with a solvent and recovered.

11. The filtrate from step 10, consisting essentially of a solvent, ethylene glycol and water, is heated to evaporate a part of the solvent.

12. The solution remaining from step 11, consisting essentially of ethylene glycol and water is then distilled to separate the ethylene glycol from the water. The ethylene glycol so provided may be used for its customary uses.

If it is not desired to recover the ethylene glycol, the process can be stopped after step 7 above.

DESCRIPTION OF THE PREFERRED EMBODIMENTS

In the practice of the invention the still bottoms are first analyzed to determine their terephthalic acid content. Thereafter, and if necessary, water is added to adjust the still bottom content so that the total amount of water present, original water, plus added water will be approximately ten times the amount of terephthalic acid present. Less water may be used, however, this makes the final filtration of the terephthalic acid more difficult. If more water is used it increases the amount of water to be separated from the glycol, which increases the ulitmate cost. For the successful, economical practice of the invention the terephthalic acid/water relationship should not be substantially varied.

In order to determine the terephthalic acid content of a still bottom product that is to be treated conventional techniques may be employed as, for example, hydrolyzing the still bottom in a substantial amount of water using sodium hydroxide in a pH of approximately 8.5 and at a temperature of approximately 185° F. to 212° F. After the hydrolization is complete, the material is filtered and the filtrate acidified to a pH of about 1 to 3 to precipitate the terephthalic acid. The precipitated therephthalic acid is then filtered, washed, dried and weighed. Still bottoms, as they are produced in the manufacture of polyethylene terephthalate resins, are waxy, granular masses. Their water content as produced is negligible for the purposes of this invention. However, in order to ship and handle the still bottoms water is frequently added. The amount of water added should be noted so that it can be determined whether and how much additional water must be added.

Two representative examples of still bottom materials that may be treated in accordance with the invention have been analyzed and found to contain the following ingredients.

| STILL BOTTOM A | % by weight |
|---|---|
| Water | 26% |
| Solids | 32% |
| Ethylene Glycol, Di Ethylene Glycol, and Tri Ethylene Glycol | 42% |
| Antimony | 7200 PPM |
| Sodium | 4300 PPM |

(Sodium found in the material was sodium hydroxide which had been added to enhance the handling characteristics of the material.)

| STILL BOTTOM B | % by weight |
|---|---|
| Water | 37.6 |
| Solids | 31.6 |
| Ethylene Glycol, Di Ethylene Glycol, and Tri Ethylene Glycol | 30.8 |
| Antimony | 5800 PPM |
| Sodium | 23,000 PPM |

To 1,000 grams of still bottom "B" which, by the method described above, was determined to contain approximately 200 grams of terephthalic acid, was added 1624 grams of water to obtain a total water content of 2,000 grams, an amount equal to ten times the TPA content. The product contained 376 grams of water added for handling purposes. While more or less water can be utilized, this is the preferred amount. More water will increase the cost of subsequent glycol removed, while less water will decrease the efficiency of the terephthalic acid filtration.

The still bottoms and water were heated to about 190° F. Lower temperatures would increase the time required. After the temperature was brought to about 190° F. a sufficient amount of sodium hydroxide (50%) was added to obtain a pH of about 8.5. The amount required was about 120 grams, and added at a rate to maintain the solution between 8 and 8.5 pH. It has been found that when the solution stabilized between 8 and 8.5 pH, the desired hydrolysis had been completed.

Next, dilute sulfuric acid was added to the mixture in sufficient quantity to lower the pH of the solution to 6.2–6.5. The pH range has been found to be one where the antimony compound(s) is the least soluble. It has also been found that if the pH is lowered below this range undesirable precipitation of the terephthalic acid occurs. The mixture, with precipitated antimony compound(s), was filtered to remove the antimony compound(s). Such compound(s) were then dried. They may be reused, as for example, by returning them to an antimony producer. The filtrate remaining contained about 250 PPM antimony, still above desirable levels.

It was found that in order to obtain terephthalic acid without color contamination that the filtrate should next be filtered through activated carbon. About 20 grams was required. Not only does this improve the quality of the terephthalic acid but it also removes additional antimony compound(s) thought to be combined with some of the color contaminates.

To the filtrate was added a sufficient amount of sulfuric acid to lower the pH to about 2. This was approximately 170 grams of 96% sulfuric acid. The mixture's temperature was maintained at about 170° F. for about 30 minutes. During this time terephthalic acid precipitated from the filtrate. It was subsequently filtered and washed with deionized water which may be reused. The terephthalic acid recovered, amounting to 200 grams, was pure and could have been reused if desired for its customary usage, as for example, for making polyester resins.

To the filtrate, maintained at a temperature of about 180° F. and at a pH of about 2, was added approximately 25 grams of sodium thiosulfate. The temperature was raised and maintained at about 180°–212° F., under agitation for 15 minutes to 30 minutes. During this period the sodium thiosulfate reacted with the antimony compound(s) to form an insoluble antimony sulfide precipitate. The precipitate formed in the preceding step was removed by filtration. The precipitate was then dried and may be used, as example, by returning it to an antimony producer. The filtrate showed that only about two to three PPM soluble antimony remained in the filtrate, an amount within the acceptable safety range.

The subsequent steps relate to the recovery of the glycol fraction of the mixture. Under certain situations such a recovery may not be deemed necessary and the filtrate can be discarded. Also it may be possible in some applications to reuse the filtrate in this form or after filtering. The following steps provide a suitable way in which to recover the glycol fraction. Obviously, those skilled in the art may choose to employ other means for accomplishing the recovery.

The temperature of the filtrate was raised to about 180° to 212° F. and approximately one-half of the water was removed.

To the filtrate was added sodium hydroxide (50%) to adjust the pH to about 6.5 to 8. The filtrate was then passed through a carbon tower containing about ten grams of activated carbon. In addition to the glycol there is also sodium sulfate present. To this solution was added about 2 parts alcohol and the mixture agitated. Sodium sulfate was precipitated and separated by filtration. About 100 grams of alcohol were used to wash the sodium sulfate and the sodium sulfate was dried and was of a quality that may be used in commerce.

About one-half of the alcohol was removed by heating the filtrate to evaporate the alcohol. The remaining solution was then subjected to a final distillation step to separate the alcohol, glycols, and water. The glycols were found to be of such purity that they could be reused in commerce.

Those skilled in the art will recognize that various modifications may be made in the process previously described. For example, and without limitation, the alkaline hydrolysis step may be carried out with bases other than sodium hydroxide, as for example, ammonium hydroxide. And, acids other than sulfuric may be utilized, as for example, phosphoric. Also, the sequence of the steps may be varied under some conditions.

Having thus described our invention, we claim:

1. A recovery method for polyester still bottoms which includes polyester materials, antimony compounds, terephthalic acid, and glycols, comprising:

A. subjecting the still bottoms to an alkaline hydrolysis step, the amount of water in step (A) being about 10 parts by weight of water for each part of terephthalic acid present, said alkali hydrolysis step carried out at a temperature of about 185° to 212° F. and at a pH of between about 8 to 8.5, B. acidifying the material from step (A) to a pH of about 6.2 to 6.5 to precipitate a portion of the antimony compounds therefrom, C. removing the precipitated antimony compounds and treating the unprecipitated material with activated carbon, D. acidifying the unprecipitated material from step (B) at a temperature of about 170° F. to a pH of about 1 to 3 to precipitate terephthalic acid, E. removing the precipitated terephthalic acid, F. adding a sufficient quantity of sodium thiosulfate to precipitate substantially all of the remaining antimony compounds, the temperature at which the mixture is maintained being about 180° to 212° F., G. removing the precipitated antimony compounds.

2. The recovery method of claim 1 wherein sulfuric acid is used in step (B) to acidify the material from step (A).

3. The recovery method of claim 2 wherein the acidification is carried out at about 170° F.

4. The recovery method of claim 1 wherein glycol is recovered from the solution remaining after step (G).

5. The recovery method of claim 4 wherein the glycol recovery method comprises the steps of H. removing about one-half of the water after step (G) at a temperature of about 180° to 212° F., I. adjusting the solution remaining after step (H) to a pH of about 6.5 to 8 and treating it with activated carbon, J. adding about two parts by weight per part of alcohol to the solution remaining after step (I) to precipitate sodium sulfate and removing the sodium sulfate so precipitated, K. evaporating a portion of the alcohol, and L. separating glycol from the solution of step (K) by distillation.

* * * * *